United States Patent [19]

Husbands et al.

[11] Patent Number: 5,530,013
[45] Date of Patent: Jun. 25, 1996

[54] VENLAFAXINE IN THE INDUCEMENT OF COGNITION ENHANCEMENT

[75] Inventors: G. E. Morris Husbands, Berwyn; Magid A. Abou-Gharbia, Glen Mills; John A. Moyer; Eric A. Muth, both of New Hope, all of Pa.

[73] Assignee: American Home Products Corporation, Madison, N.J.

[21] Appl. No.: 442,546

[22] Filed: May 16, 1995

Related U.S. Application Data

[63] Continuation-in-part of Ser. No. 384,070, Feb. 6, 1995, abandoned, which is a continuation of Ser. No. 195,417, Feb. 14, 1994, abandoned.

[51] Int. Cl.⁶ .................................................. A61K 31/41
[52] U.S. Cl. .................................................. 514/330
[58] Field of Search .................................................. 514/330

[56] References Cited

U.S. PATENT DOCUMENTS

| 3,334,091 | 7/1967 | Houlihan. | |
|---|---|---|---|
| 3,334,095 | 8/1967 | Houluhan. | |
| 4,080,449 | 3/1978 | Croisier et al.. | |
| 4,320,057 | 3/1982 | Freed et al.. | |
| 4,391,752 | 7/1983 | Crossley. | |
| 4,399,136 | 8/1983 | Hassall et al. | 424/250 |
| 4,415,496 | 11/1983 | Harris et al.. | |
| 4,487,929 | 12/1984 | Hassall et al. | 544/244 |
| 4,512,924 | 4/1985 | Attwood et al. | 260/243.3 |
| 4,584,294 | 4/1986 | Ruyle | 514/214 |
| 4,658,024 | 4/1987 | Attwood et al. | 540/500 |
| 4,692,438 | 9/1987 | Hassall et al. | 514/183 |
| 4,716,232 | 12/1987 | Ternansky | 548/364 |
| 4,734,504 | 3/1988 | Holmes | 548/364 |
| 4,734,505 | 3/1988 | Holmes | 548/364 |
| 4,762,924 | 8/1988 | Hassall et al. | 540/501 |
| 4,772,701 | 9/1988 | Attwood et al. | 546/235 |
| 4,782,149 | 11/1988 | Lawton et al. | 540/500 |
| 4,785,093 | 11/1988 | Hassall et al. | 544/244 |
| 4,808,713 | 2/1989 | Attwood et al. | 540/487 |
| 4,824,832 | 4/1989 | Flynn et al. | 540/496 |
| 4,826,980 | 5/1989 | Hassall et al. | 544/244 |
| 4,973,585 | 11/1990 | Flynn et al. | 514/214 |
| 4,999,370 | 3/1991 | Ruger et al. | 514/412 |
| 5,043,346 | 8/1991 | Hock et al. | 514/409 |
| 5,208,230 | 5/1993 | Flynn et al. | 514/214 |
| 5,238,932 | 7/1994 | Flynn et al. | 514/214 |

FOREIGN PATENT DOCUMENTS

| 0128728 | 12/1984 | European Pat. Off.. |
|---|---|---|
| 0249223 | 12/1987 | European Pat. Off.. |
| 0249224 | 12/1987 | European Pat. Off.. |
| 0322914 | 12/1988 | European Pat. Off.. |
| 9109840 | 7/1991 | European Pat. Off.. |
| 0481522 | 4/1992 | European Pat. Off.. |
| 0492369 | 7/1992 | European Pat. Off.. |
| 0533084 | 9/1992 | European Pat. Off.. |
| 0599444 | 6/1994 | European Pat. Off.. |
| 9108195 | 6/1991 | WIPO. |
| 9302099 | 2/1993 | WIPO. |

OTHER PUBLICATIONS

Medline Abstract 93002114, Saleta et al., "Pharmacodynamics of Venlalaxine evaluated by EEG brain mapping, psychimitry, and psychophysiology" Br. J. Clin. Pharm Jun. 1992 33(6) 589–601. Abstract only.

Flynn, et al., J. Am. Chem. Soc. 109, 7914 (1987).

Flynn, et al., Peptide Chemistry (1987); T. Shiba & Sakakibara (ed.), Protein Research Foundation, Osaka (1988).

Flynn, et al., Tetrahedron Letters, vol. 31 (6), 815–88 (1990).

Attwood, et al., J. Chem. Soc. Perkin Trans. I, pp. 1011–1019 (1986).

(List continued on next page.)

Primary Examiner—Raymond Henley, III
Assistant Examiner—Keith MacMillan
Attorney, Agent, or Firm—Steven R. Eck

[57] ABSTRACT

This invention provides a method of inducing cognition enhancement in a mammal by administering to the mammal experiencing a cognition impairment an effective amount of a hydroxycycloalkanephenethyl amine compound of the following structural formula:

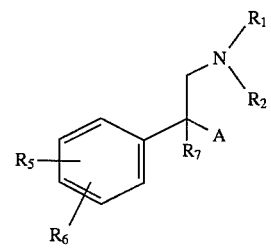

in which A is a moiety of the formula

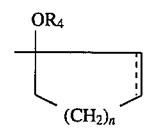

wherein the dotted line represents optional unsaturation;

$R_1$ is hydrogen or alkyl;

$R_2$ is alkyl;

$R_4$ is hydrogen, alkyl, formyl, or alkanol;

$R_5$ and $R_6$ are, independently, hydrogen, hydroxyl, alkyl, alkoxy, alkanoyloxy, cyano, nitro, alkylmercapto, amino, alkylamino, dialkylamino, alkanamido, halo, trifluoromethyl, or taken together, methylene dioxy;

$R_7$ is hydrogen or alkyl; and n is 0, 1, 2, 3, or 4;
or a pharmaceutically acceptable salt thereof.

14 Claims, No Drawings

OTHER PUBLICATIONS

Natoff, et al., Drugs of the Future, vol. 12 (5): 475–483 (1987).

Journal of Am. Coll. of Card. vol. 17, No. 6, pp. 137B–142B (May 1991).

Supplement I Cir. vol. 86(4) pp. 1–220(0873) (Oct. 1992).

J. Med. Chem. 1992, 35, 823–832, Timothy D. Ocain et al.

Bioorganic and Medical Chem. Letters vo. 1, 309, 1991.

Burkholder, et al. *Bioorganic and Medical Chem. Letters*, vol. 3, No. 2, pp. 231–234, 1992.

Flynn et al., *J. Med. Chem.* 1993, 36 2420–242.

Fournie-Zaluski, Marie-Claude et al., *J. Med. Chem.*, 1992 vol. 35, pp. 2473–2481.

Fournie-Zaluski, Marie-Claude et al., *J. Med. Chem.*, 1992 vol. 35, pp. 1259–1266.

French, John F., *Jour. of Pharm and Exper. Therapeutics*, vol. 268, No. 1, pp. 180–186, 1993.

W. H. Parsons et al., *Biochemical and Biophysical Research Communications* vol. 117, No. 1, 1993 (Nov. 30, 1983).

VENLAFAXINE IN THE INDUCEMENT OF COGNITION ENHANCEMENT

RELATED APPLICATIONS

This is a continuation-in-part of co-pending application Ser. No. 08/384,070, filed Feb. 6, 1995, now abandoned which is a continuation of application Ser. No. 08/195,417, filed Feb. 14, 1994, now abandoned.

This invention comprises a new use for venlafaxine. More particularly, this invention comprises a method for inducing cognition enhancement in a mammal.

BACKGROUND OF THE INVENTION

The active ingredients of this invention, (1-[2-(dimethylamino)-1-(4-methoxyphenyl)ethyl]cyclohexanol), its analogues or therapeutically acceptable salts thereof, are known generally as venlafaxine. These ingredients are disclosed in U.S. Pat. No. 4,535,186 (Husbands et al.) and have been previously reported to be useful as an antidepressant. U.S. Pat. No. 4,535,186 teaches the production of venlafaxine and its analogues and is incorporated herein by reference. For the purposes of this disclosure and the claims that follow, it is understood that the use of venlafaxine includes the use of venlafaxine's free base, its pharmaceutically acceptable salts, its racemate and its individual enantiomers, and venlafaxine analogs, both as racemates and as their individual enantiomers.

Venlafaxine has been shown to be a potent inhibitor of monoamine neurotransmitter uptake, a mechanism associated with clinical antidepressant activity. Due to its novel structure, venlafaxine has a mechanism of action unrelated to other available antidepressants, such as the tricyclic antidepressants desipramine, nortriptyline, protriptyline, imipramine, amitryptyline, trimipramine, and doxepin.

It is believed that venlafaxine's mechanism of action is related to potent inhibition of the uptake of the monoamine neurotransmitters serotonin and norepinephrine. To a lesser degree, venlafaxine also inhibits dopamine reuptake, but it has no inhibitory activity on monoamine oxidase. O-desmethylvenlafaxine, venlafaxine's major metabolite in humans, exhibits a similar pharmacologic profile. Venlafaxine's ability to inhibit norepinephrine and serotonin (5-HT) uptake has been predicted to have an efficacy which rivals or surpasses that of tricyclic antidepressants (Stuart A. Montgomery, M.D., J. Clin. Psychiatry, 54:3, March 1993).

In contrast to classical tricyclic antidepressant drugs, venlafaxine has virtually no affinity for muscarinic, histaminergic, or adrenergic receptors in vitro. Pharmacologic activity at these receptors is associated with the various anticholinergic, sedative and cardiovascular effects seen with the tricyclic antidepressant drugs.

DESCRIPTION OF THE INVENTION

The present invention provides a method for inducing cognition enhancement in a mammal, preferably in a human. This invention may also be referred to as a method of treating cognitive impairment in a mammal, preferably in a human, such as, but not limited to the cognitive impairments caused by dementias, Alzheimer's-type Dementia, Parkinson's Disease and Age Associated Memory Impairment. Symptoms of such cognition-depleting maladies may include varying reductions in concentration, judgement, memory and orientation.

In accordance with the present invention there is provided a method of inducing cognition enhancement in a mammal, preferably in a human. This method involves administering to the mammal one or more compounds from a group of substituted phenethylamines. The compounds utilized with this invention present the following structural formula:

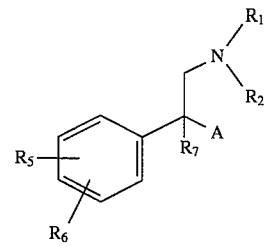

in which A is a moiety of the formula

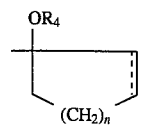

wherein
the dotted line represents optional unsaturation;
$R_1$ is hydrogen or alkyl of 1 to 6 carbon atoms;
$R_2$ is alkyl of 1 to 6 carbon atoms;
$R_4$ is hydrogen, alkyl of 1 to 6 carbon atoms, formyl, or alkanol of 2 to 7 carbon atoms;
$R_5$ and $R_6$ are independently hydrogen, hydroxyl, alkyl of 1 to 6 carbon atoms, alkoxy of 1 to 6 carbon atoms, alkanoyloxy of 2 to 7 carbon atoms, cyano, nitro, alkylmercapto of 1 to 6 carbon atoms, amino, alkylamino of 1 to 6 carbon atoms, dialkylamino in which each alkyl group is of 1 to 6 carbon atoms, alkanamido of 2 to 7 carbon atoms, halo, trifluoromethyl, or when taken together, methylene dioxy; $R_7$ is hydrogen or alkyl of 1 to 6 carbon atoms; and n is one of the integers 0, 1, 2, 3, or 4;
or a pharmaceutically acceptable salt thereof.

The preferred compounds are those of the formula:

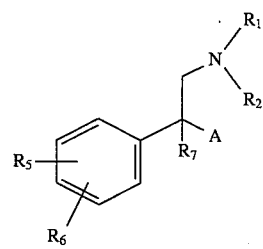

in which
A is as defined supra;
$R_1$ is hydrogen or alkyl of 1 to 3 carbon atoms;
$R_2$ is alkyl of 1 to 3 carbon atoms;
$R_3$ is hydrogen, hydroxy, alkoxy of 1 to 3 carbon atoms, chloro, bromo, trifluoromethyl or alkyl of 1 to 3 carbon atoms;
$R_5$ is hydrogen, hydroxyl, alkoxy of 1 to 3 carbon atoms, chloro, bromo, trifluoromethyl or alkyl of 1 to 3 carbon atoms;
$R_6$ is alkyl of 1 to 3 carbon atoms, alkoxy of 1 to 3 carbon atoms, chloro, bromo, trifluoromethyl or alkanoyloxy of 2 to 3 carbon atoms;
$R_7$ is hydrogen or alkyl of 1 to 3 carbon atoms;
or a pharmaceutically acceptable salt thereof.

The most preferred compounds are those in which both $R_5$ and $R_6$ are in meta positions, or one of $R_5$ and $R_6$ is in the para position, and n is 2.

Of particular interest are the compounds 1-[(2-dimethylamino)-1-(4-methoxyphenyl)ethyl]cyclohexanol and 1-[(2-dimethylamino)-1-(4-hydoxyphenyl)ethyl]cyclohexanol and pharmaceutically acceptable salts thereof.

The compounds in which $R_4$ is formyl or alkanoyl of 2 to 7 carbon atoms have been found to be not as potent as the corresponding free hydroxy bearing derivatives. However, in long term therapy the acyloxy derivatives will act as pro drugs as the acyl group is removed in vivo either via acid hydrolysis in the stomach or enzymatically.

The pharmaceutically acceptable acid addition salts of the basic compounds of this invention are formed conventionally by reaction of the free base with an equivalent amount of any acid which forms a non-toxic salt. Illustrative acids are either inorganic or organic, including hydrochloric, hydrobromic, fumaric, maleic, succinic, sulfuric, phosphoric, tartaric, acetic, citric, oxalic, and similar acids. For parenteral administration, the use of water soluble salts is preferred, although either the free base of the pharmaceutically acceptable salts are applicable for oral or parenteral administration of the cognition enhancing agents of this invention. The halo substituent representing $R_5$ or $R_6$ is intended to include the chloro, bromo, iodo, or fluoro substituents.

Pharmaceutical compositions containing the compounds of this invention represent an additional aspect of this invention. The active ingredient can be compounded into any of the usual oral dosage forms including tablets, capsules and liquid preparations such as elixirs and suspensions containing various coloring, flavoring, stabilizing and flavor masking substances. For compounding oral dosage forms, the active ingredient can be mixed with various conventional tabletting materials such as starch, calcium carbonate, lactose, sucrose and dicalcium phosphate to aid the tabletting or capsulating process. Magnesium stearate, as an additive, provides a useful lubricant function when desired.

The active ingredients can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can often be dissolved in a suitable organic solvent, for instance aqueous propylene glycol or polyethylene glycol solutions. Aqueous propylene glycol containing from 10 to 75% of the glycol by weight is generally suitable. In other instances other compositions can be made by dispersing the finely-divided active ingredient in aqueous starch or sodium carboxymethyl cellulose solution, or in a suitable oil, for instance arachis oil. Liquid pharmaceutical compositions which are sterile solutions or suspensions can be utilized by intramuscular, intraperitoneal or subcutaneous injection.

Preferably the pharmaceutical composition is in unit dosage form, e.g. as tablets or capsules. In such form, the composition is sub-divided in unit doses containing appropriate quantities of the active ingredient; the unit dosage forms can be packaged compositions, for example, packeted powders or vials or ampoules. The unit dosage form can be a capsule, cachet or tablet itself, or it can be the appropriate number of any of these in package form. The quantity of the active ingredient in a unit dose of composition may be varied or adjusted from about 2 mg. or less to about 50 mg. or more, according to the particular need and the activity of the active ingredient. The usual oral recommended dose of venlafaxine for humans may be between about 75 and about 200 mg/day and this dose may be administered in divided doses, preferably with food if administered orally. A maximum recommended daily dose for humans would be about 375 mg. It will be understood by one skilled in the art that doseage under this invention will be determined by the particular circumstances surrounding each case, as will the route of administration.

It should also be understood that the present invention is intended to include all methods of, and reasons for, inducing cognition enhancement in a mammal by administering to the mammal an effective amount of venlafaxine or its analogues or pharmaceutically acceptable salts. For the purposes of the present invention, inducing cognition enhancement is to be understood as covering all prophylactic, therapeutic, progression inhibiting, remedial, maintenance, curative or other administrations, regimens or treatments of or with venlafaxine or its analogues or salts that yield the desired cognition enhancing effects in a mammal.

The following examples are provided to demonstrate the efficacy of venlafaxine in the production of cognitive enhancing qualities in a mammal. It is understood that this example is merely illustrative and is not intended to limit the scope of the present invention.

EXAMPLE 1

To establish venlafaxine's cognition enhancement properties, it was tested in the scopolamine-impaired radial arm maze test. In this test, a reduction in scopolamine impairment of memory is indicative of cognitive enhancement.

Materials and Methods

Animals

Male Sprague-Dawley, CD rats (Charles River, Kingston, N.Y.) weighing 200–250 g on arrival were used. For one week, the rats were housed, six per cage, with standard laboratory chow and water available ad libitum. Housing was in a colony room maintained at 22° C. and had a 12 hour light/dark cycle with lights on at 6:00 AM. Following habituation to the facility, animals were individually housed and maintained at 85% of free-feeding weight (Results® precision pellets, Bio-Serv, Frenchtown, N.J.). Once stable weights were attained, the rats were acclimated to the 8-arm radial maze.

Materials

The structure of the maze was an adaptation from that of Peele and Baron (Pharmacology, Biochemistry, and Behavior, 29:143–150, 1988). The maze was elevated to a height of 75.5 cm and composed of a circular area surrounded by 8 arms radiating away from the center, equidistant from one another. Each arm was 58 cm long×13 cm high. A clear plexiglass cylinder was lowered to enclose the animal in the center portion of the maze prior to the start of each session. Each arm of the maze was equipped with 3 sets of photocells interfaced to a data acquisition unit (Hewlett Packard 2497A), which in turn was interfaced to an HP Vectra ES/12. The photocells were used to track the movement of the rat in the maze. Coulburn Pellet Feeders (E14-12) located above food cups at the end of each arm, dispensed two 45 mg chocolate pellets (Bio-Serv) when the outer photocell of the arm was activated for the first time in a given session. An in-house program compiled and stored the data. The maze was located in a testing room with black and white geometric posters on each wall to serve as visual cues. During all training and testing procedures, white noise was audible (~70 db).

Procedure

The training procedure consisted of five phases, each with daily sessions lasting 5 or 10 minutes. A 10 second delay was imposed between the time the rat was placed in the center portion of the maze and when the cylinder was raised to begin the session. During Phase 1, food-restricted pairs of rats were placed on the maze for 10 minutes with 45 mg chocolate food pellets scattered throughout the 8 arms of the maze. During Phase II, each rat was placed individually on the maze for a 10 minute period, with pellets scattered from the middle photocell to the food cup of each arm. During Phase III, each rat was placed on the maze for a 10 minute period, with food pellets located only in and around the food cups in each arm. In Phase IV, each rat was allowed 10 minutes to collect two pellets from each arm. Re-entry into an arm was considered an error. Rats were trained daily in this manner until they achieved criterion performance with $\leq 2$ total errors on three consecutive days of training. Total habituation and training time was approximately 3 weeks.

Drug Preparation

Venlafaxine was prepared in phosphate buffered saline and administered in a volume of 1 ml/kg. Scopolamine HBr (0.3 mg/kg s.c.) served as the impairing agent, producing an increase in error rate (loss of memory). In preliminary experiments it was determined that 10 mg/kg i.p. of venlafaxine was the highest dose of the drug which, in combination with scopolamine (0.3 mg/kg s.c.), was tolerated by the rats, as evidenced by appropriate completion of the test. In the experiments reported here, venlafaxine (1, 3, 10 mg/kg i.p.) was given intraperitoneally simultaneously with scopolamine, 30 minutes prior to the first maze exposure on any given test day.

Statistical Design

To assess venlafaxine, an 8×8 balanced latin square for repeated measures was designed, in order to achieve a high experimental efficiency with the least amount of animals. Eight experimental sessions, two per week, were conducted with the 8 treatments (vehicle, scopolamine, 3 doses of venlafaxine in combination with scopolamine) randomized within each session. Each treatment followed every other treatment the same number of times. Therefore, the residual effect of every treatment could be estimated and removed from the direct treatment effect. Following ANOVA, multiple comparisons were performed using Dunnett's two-sided test on adjusted means.

Animals that did not make 4 correct choices within 5 minutes during the first exposure, or that had not made a total of 8 choices by the end of the 2nd exposure, were considered to have "timed-out" for that session. Any animal that "timed-out" following administration of more than one dose of venlafaxine was excluded from the analysis.

Results

Venlafaxine (3.0 mg/kg i.p.) produced significant reductions in scopolamine impairment. The 10 mg/kg i.p. dose of venlafaxine also attenuated the scopolamine impairment, since this group did not differ significantly from vehicle-treated (i.e., no scopolamine) animals.

In order to estimate $ED_{50}$ values for the effects of venlafaxine on the scopolamine impairment, dose-response curves were fit to the mean error dam. To fit these curves, the effect of scopolamine by itself was used as an indication of the maximum impairment (upper asymptote of curves). Since there was no drug effect on this condition, the drug effect was considered to be 0%. The 3 mg/kg dose of venlafaxine produced the largest degree of reduction in the scopolamine impairment (lower asymptote of curves) and was used as an indication of the maximum (i.e., 100%) drug effect. $ED_{50}$ values were then estimated graphically to be 1 mg/kg i.p. for venlafaxine. As a comparison, idebenone was determined to have an $ED_{50}$ value of 3 mg/kg i.p.

EXAMPLE 2

In a second test, rats were first trained to th criteria in the 8-arm radial maze as for the scopolamine impairent study described above. Under appropriate anesthesia, using stereotaxic procedures, AF64A, ethylcholine mustard aziridinium ion, a selective cholinergic toxin was injected intracerebroventricularly (3 nmol per side in 3 μl). After one month of recovery the rats ere retested on the maze and determined to be impaired.

The rats were administered venlefaxine 1, 3 or 10 mg/kg/day by osmotic minipumps, inserted subcutaneously, over a two-week period. During each two-week infusion period, maze performance was assessed on days 2, 5, 9 and 14. Baseline performance assessed for each rat prior to each dosing. In each experiment, two control groups were also assessed; one group of AF64A-impaired rats was not treated with venlafaxine and a second group of unimpaired rats was subjected to surgery, except that no AF64A was administered. As expected, both the AF64A-only and venlefaxine-treated groups made more errors than the vehicle control group on each test day.

No apparent beneficial effect of venlefaxine treatment was seen in the venlefaxine-treated rats at doses of either 1 or 10 mg/kg/day, but beneficial effects of venlefaxine treatment were seen in the group receiving 3 mg venlefaxine/kg/day. The lack of effect of venlafaxine in this paradigm when delivered at either 1 or 10 mg/kg/day was not unexpected as this type of U-shaped dose-response curve has been demonstrated before for the cholinergic agonist arecoline.

This demonstrated positive effect of venlafaxine at 3 mg/kg/day is of particular significance concerning the treatment of cognition enhancement because of the neurological activity of AF64A. Unlike that of scopolamine, AF64A impairment parallels the cholinergic hypofunction seen in Alzheimer's patients because AF64A acts as a neurotoxin to destroy cholinergic neurons in its recipients.

What is claimed:

1. A method of inducing cognition enhancement in a mammal experiencing cognition impairment, the method comprising administering to the mammal experiencing cognition impairment an effective amount of a compound of the formula:

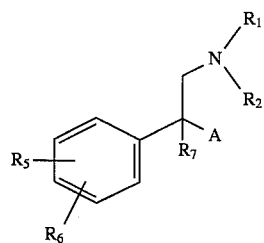

in which A is a moiety of the formula

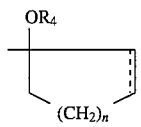

wherein
the dotted line represents optional unsaturation;
$R_1$ is hydrogen or alkyl of 1 to 6 carbon atoms;
$R_2$ is alkyl of 1 to 6 carbon atoms;
$R_4$ is hydrogen, alkyl of 1 to 6 carbon atoms, formyl, or alkanol of 2 to 7 carbon atoms;
$R_5$ and $R_6$ are, independently, hydrogen, hydroxyl, alkyl of 1 to 6 carbon atoms, alkoxy of 1 to 6 carbon atoms, alkanoyloxy of 2 to 7 carbon atoms, cyano, nitro, alkylmercapto of 1 to 6 carbon atoms, amino, alkylamino of 1 to 6 carbon atoms, dialkylamino in which each alkyl group is of 1 to 6 carbon atoms, alkanamido of 2 to 7 carbon atoms, halo, trifluoromethyl, or taken together, methylene dioxy;
$R_7$ is hydrogen or alkyl of 1 to 6 carbon atoms; and
n is 0, 1, 2, 3, or 4;
or a pharmaceutically acceptable salt thereof.

2. The method of claim 1 in which the mammal is a human.

3. The method of claim 1 wherein the compound of the formula:

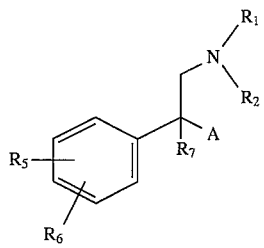

in which A is a moiety of the formula

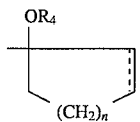

wherein
the dotted line represents optional unsaturation, and
$R_1$ is hydrogen or alkyl of 1 to 3 carbon atoms;
$R_2$ is alkyl of 1 to 3 carbon atoms;
$R_5$ is hydrogen, hydroxyl, alkoxy of 1 to 3 carbon atoms, chloro, bromo, trifluoromethyl or alkyl of 1 to 3 carbon atoms;
$R_6$ is alkyl of 1 to 3 carbon atoms, alkoxy of 1 to 3 carbon atoms, chloro, bromo, trifluoromethyl or alkanoyloxy of 2 to 3 carbon atoms.
$R_7$ is hydrogen or alkyl of 1 to 3 carbon atoms;
or a pharmaceutically acceptable salt thereof.

4. The method of claim 3 wherein $R_5$ and $R_6$ are both in meta positions, or one of $R_5$ and $R_6$ is in the para position, and n is 2.

5. The method of claim 3 wherein the compound is 1-[(2-dimethylamino)-1-(4-methoxyphenyl)ethyl]cyclohexanol or a pharmaceutically acceptable salt thereof.

6. The method of claim 3 wherein the compound is 1-[2-(dimethylamino)-1-(4-hydroxyphenyl)ethyl]cyclohexanol or a pharmaceutically acceptable salt thereof.

7. The method of claim 3 in which the mammal is a human.

8. The method of claim 1, wherein the effective amount comprises a daily dose of between about 50 mg/day and about 375 mg/day.

9. The method of claim 1 wherein the effective amount comprises a daily dose of between about 75 mg/day and about 200 mg/day.

10. The method of claim 3 wherein the effective amount comprises a daily dose of between about 50 mg/day and about 375 mg/day.

11. The method of claim 3 wherein the effective amount comprises a daily dose of between about 75 mg/day and about 200 mg/day.

12. The method of claim 1 wherein the cognition impairment is caused by Alzheimer's -type Dementia.

13. The method of claim 1 wherein the cognition impairment is caused by Parkinson's Disease.

14. The method of claim 1 wherein the cognition impairment is caused by Age Associated Memory Impairment.

* * * * *